(12) United States Patent
Pekander et al.

(10) Patent No.: US 10,646,145 B2
(45) Date of Patent: May 12, 2020

(54) REFLECTIVE SPO₂ MEASUREMENT SYSTEM AND METHOD

(71) Applicant: General Electric Company, Schenectady, NY (US)

(72) Inventors: Otto Valtteri Pekander, Helsinki (FI); Matti Huiku, Helsinki (FI); Juha Virtanen, Helsinki (FI)

(73) Assignee: General Electric Company, Schenectady, NY (US)

( * ) Notice: Subject to any disclaimer, the term of this patent is extended or adjusted under 35 U.S.C. 154(b) by 71 days.

(21) Appl. No.: 15/893,285

(22) Filed: Feb. 9, 2018

(65) Prior Publication Data

US 2019/0246967 A1  Aug. 15, 2019

(51) Int. Cl.
*A61B 5/1455* (2006.01)
*A61B 5/00* (2006.01)
*A61B 5/1495* (2006.01)

(52) U.S. Cl.
CPC ........ *A61B 5/14552* (2013.01); *A61B 5/1495* (2013.01); *A61B 5/7264* (2013.01)

(58) Field of Classification Search
CPC .................................................. A61B 5/14552
USPC ........................................................ 356/410
See application file for complete search history.

(56) References Cited

U.S. PATENT DOCUMENTS

| | | |
|---|---|---|
| 5,355,882 A | 10/1994 | Ukawa et al. |
| 6,151,107 A | 11/2000 | Schollermann et al. |
| 6,987,994 B1 | 1/2006 | Mortz |
| 2004/0024297 A1* | 2/2004 | Chen ................... A61B 5/14553 600/323 |
| 2008/0081966 A1* | 4/2008 | Debreczeny ....... A61B 5/14552 600/310 |
| 2009/0018405 A1* | 1/2009 | Katsumura ............ A61B 5/024 600/301 |
| 2009/0030296 A1* | 1/2009 | Sterling ............. A61B 5/14551 600/323 |

(Continued)

OTHER PUBLICATIONS

Lee et al., "Reflectance pulse oximetry: Practical issues and limitations", The Korean Institute of Communications Information Sciences, 2016, 195-198.

*Primary Examiner* — Tarifur R Chowdhury
*Assistant Examiner* — Omar H Nixon
(74) *Attorney, Agent, or Firm* — Andrus Intellectual Property Law, LLP

(57) ABSTRACT

A reflective SpO₂ measurement system includes a light source that emits light of at least a first and second wavelengths, and one or more detection devices forming a close detector positioned at a first distance from the light source and a far detector positioned at a second distance from the light source, wherein the second distance is greater than the first. The SpO₂ measurement system is configured to operate in a high power mode to determine a calibration factor based on the comparison of light reflections detected by the close detector and the far detector. The system is further configured to operate in a low power mode to generate a low intensity light pulse, and detect a close reflection of the low intensity light pulse with the close detector. An SpO₂ is then determined based on the close reflection of the low intensity light pulse and the calibration factor.

20 Claims, 4 Drawing Sheets

(56) References Cited

U.S. PATENT DOCUMENTS

| | | | |
|---|---|---|---|
| 2009/0247849 A1* | 10/2009 | McCutcheon | A61B 5/14551 600/323 |
| 2010/0016689 A1* | 1/2010 | Kanayama | A61B 5/14532 600/316 |
| 2011/0224518 A1* | 9/2011 | Tindi | A61B 5/14552 600/323 |
| 2012/0053432 A1 | 3/2012 | Huiku et al. | |
| 2013/0158412 A1* | 6/2013 | Hayman | A61B 5/14552 600/476 |
| 2013/0324816 A1* | 12/2013 | Bechtel | A61B 5/742 600/331 |
| 2014/0288435 A1* | 9/2014 | Richards | A61B 5/02427 600/479 |
| 2015/0057511 A1* | 2/2015 | Basu | A61B 5/02433 600/323 |
| 2015/0190063 A1* | 7/2015 | Zakharov | A61B 5/14551 600/301 |
| 2015/0238672 A1* | 8/2015 | Barrett | A61M 1/3621 356/40 |
| 2015/0366455 A1* | 12/2015 | Bezemer | A61B 5/0082 600/476 |
| 2016/0174887 A1* | 6/2016 | Kirenko | A61B 5/14552 600/332 |
| 2017/0055853 A1* | 3/2017 | Kirenko | A61B 5/02125 |
| 2017/0127988 A1* | 5/2017 | Tao | A61B 5/14552 |
| 2017/0261427 A1* | 9/2017 | Deliwala | G01N 21/3577 |
| 2017/0303861 A1* | 10/2017 | Bechtel | A61B 5/1032 |

\* cited by examiner

REFLECTIVE SPO₂ MEASUREMENT SYSTEM AND METHOD

FIELD

This invention generally relates to pulse oximeters that non-invasively measure the oxygen saturation of hemoglobin in arterial blood, and more specifically to systems and methods for reflective measurement of $SpO_2$.

Pulse oximetry is a well-established technique for measuring oxygen saturation ($SpO_2$) in arterial blood. $SpO_2$ is an important parameter, nowadays often called the fourth vital sign, which relates to the adequacy of oxygen supply to peripheral tissues and organs. Pulse oximeters provide instantaneous in-vivo measurements of arterial oxygenation, and thereby an early warning of arterial hypoxemia, for example. Pulse oximeters also display a photoplethysmographic (PPG) pulse waveform, which can be related to tissue blood volume and blood flow, i.e. the blood circulation at the site of the measurement, which is typically at the finger or ear. At present, there is a growing interest to develop portable and wearable medical sensors for various medical applications that allow the subject to move freely and thus also remote supervision of the subject. Wireless Body Area Network (WBAN) refers to short-range radio-frequency communications technologies, which are specifically suited for transmitting measurement data between different patient-worn devices. This includes battery-operated $SpO_2$ sensors.

Pulse oximetry typically uses two different light sources and a detection device, such as a photodiode. To different measurement techniques are generally used, including transmissive measurement technique where the light travels through the measurement site and is received on an opposite side of the measurement site, and a reflective measurement technique where the sensed light reflects off of the patient's tissue at the measurement site and is received by a detection device on the same side of the measurement site as the light source. Thus, transmissive measurement sensors have a light source on an opposite side of the measurement site from the detector. For reflective $SpO_2$ measurement, on the other hand, the light source and the detector are on the same side of the measurement site, and the light is reflected back at the detector by the tissue around the measurement site.

Currently, transmissive $SpO_2$ measurement is more common than reflective $SpO_2$ measurement and reflective $SpO_2$ measurement techniques are rarely used in clinical settings due to the poor accuracy of traditional reflective SpO2 sensors.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a reflective $SpO_2$ measurement system includes a light source that emits light of at least a first wavelength and a second wavelength, and one or more detection devices forming a close detector positioned at a first distance from the light source and a far detector positioned at a second distance from the light source, wherein the second distance is greater than the first. The $SpO_2$ measurement system is configured to operate in a high power mode to determine a calibration factor based on the comparison of light reflections detected by the close detector and the far detector. The system is further configured to operate in a low power mode to generate a low intensity light pulse, and detect a close reflection of the low intensity light pulse with the close detector. An $SpO_2$ is then determined based on the close reflection of the low intensity light pulse and the calibration factor.

One embodiment of a method of measuring $SpO_2$ includes generating at least one light pulse with at least one light source, wherein the at least one light pulse includes at least a first light wavelength and a second light wavelength. A close reflection of the at least one light pulse is detected with a close detector positioned at a first distance from one of the at least one light source, and a far reflection of the high intensity light pulse is detected with a far detector positioned at a second distance from one of the at least one light source, wherein the second distance is greater than the first distance. A calibration factor is then calculated based on the far reflection and the close reflection of the at least one light pulse. A low intensity light pulse is then generated with the at least one light source, wherein the low intensity light pulse contains light of the first and second wavelengths, and a close reflection of the low intensity light pulse is detected with the close detector. An $SpO_2$ is then determined based on the close reflection of the low intensity light pulse and the calibration factor.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Figure 1A:
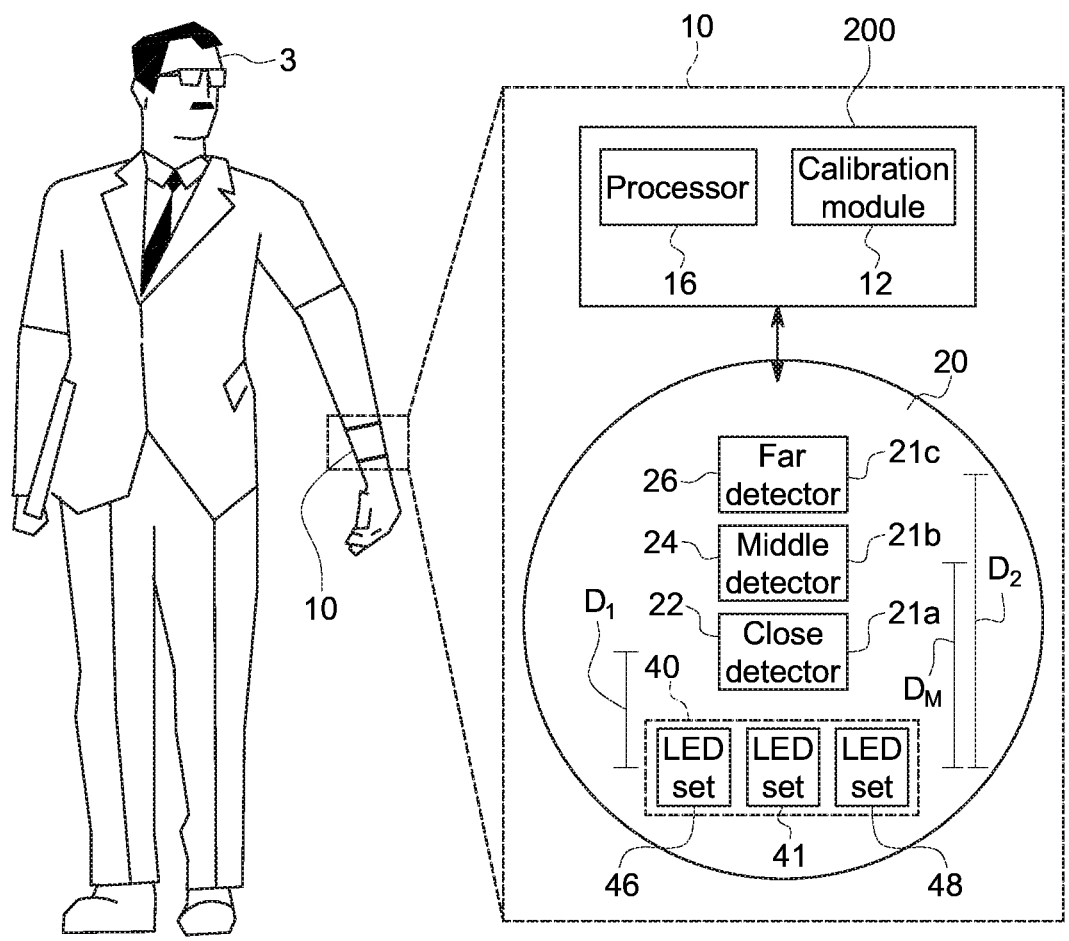
FIGS. 1A and 1B schematically depict embodiments of a reflective $SpO_2$ measurement system according to the present disclosure.

The demand for reflective pulse oximetry is increasing because it does not require a thin measurement site, such as the finger or ear. Measurement at a patient's finger may not always be possible or desirable, and $SpO_2$ measurement clips placed on a patient's finger are cumbersome and uncomfortable for a mobile patient. Furthermore, the introduction of noise due to frequent movement of the patient's hand can interfere with efficient and accurate $SpO_2$ measurement. Reflective $SpO_2$ can be conducted at a diverse range of measurement sites, including the wrists, arms, chest, forehead, and feet. For example, the inventors have recognized that reflective pulse oximeters can be devised as a wrist band or arm band to measure peripheral oxygen saturation of the blood in the arteries of the arm and/or wrist.

Through their research and experience in the relevant field, the present inventors recognized that an improved reflective $SpO_2$ sensor is needed that in enables accurate reflective $SpO_2$ measurement with relatively low power consumption. As wireless, body worn devices operate on battery power and need to be relatively small and light so as not to impede patient movement or be uncomfortable, methods and systems are needed for reducing the power consumption of the LEDs generating light for the reflective $SpO_2$ measurement. High powered light generation is generally necessary for conducting reflective $SpO_2$ measurements, as the light needs to penetrate deeply into the tissue in order to pass through the necessary arteries and reflect back to the detector. Thus, prior art reflective $SpO_2$ sensors generally have LEDs spread at a relatively far distance from the detectors sufficient for detecting the light reflecting off of deep tissues and bone in the measurement area. Furthermore, the presence of significant fatty tissue, muscle, or skin can also scatter the light, thus requiring even higher intensity light pulse in order to have an effective $SpO_2$ measurement.

Penetrating deep into the tissue at the measurement site is also necessary in order to measure oxygen levels of the arterial blood, rather than, for example, the venous blood closer to the skin. Further, blood tends to pool at locations closer to the skin, and thus shallow measurements do not provide a good representation of the overall blood oxygen level for the patient. This venous blood, pooling blood, and scattering effect of fatty tissue and muscle create an error factor for the $SpO_2$ measurement—the greater the presence of those factors, the greater the percentage of reflected light does not contribute to accurate $SpO_2$ measurement. Namely, the error factor is a value representing the amount or percentage of the reflected light caused by the error factors—venous blood, pooling blood, fatty tissue, muscle, etc.—as opposed to the reflected light that passes through arterial blood.

With currently available reflective $SpO_2$ devices and systems, obtaining a reliable $SpO_2$ measurement requires a very high intensity light pulse and significant distance between the light source and the detector. Generating that high intensity light pulse utilizes significant battery power. The relationship of the amount of light required for $SpO_2$ measurement and the distance between the light source and the detector is exponential—i.e., the amount of power required to generate a sufficient light pulse grows exponentially in relation to the increasing distance between the light source and the detector.

Upon recognition of the foregoing problems and challenges, the present inventors developed the reflective $SpO_2$ sensor, measurement system, and method that provide accurate $SpO_2$ measurement with a lower intensity light pulse by calculating a calibration factor that isolates and compensates for the effect of venous blood, fatty tissue, muscle, and other noise factors. The disclosed method and system determine a calibration factor that enables subsequent $SpO_2$ measurement using a low intensity light pulse. To determine the calibration factor, a reflective light is detected at one or more detection devices at various distances from one or more light sources. The one or more detection devices form a close detector 22 at a first distance $D_1$ from the light source 40 and a far detector 26 at a second distance $D_2$ from the light source 40. In certain embodiments, the reflective $SpO_2$ sensor 20 may further include a middle detector 24 at middle distance $D_M$ from the light source 40.

Figure 1B:
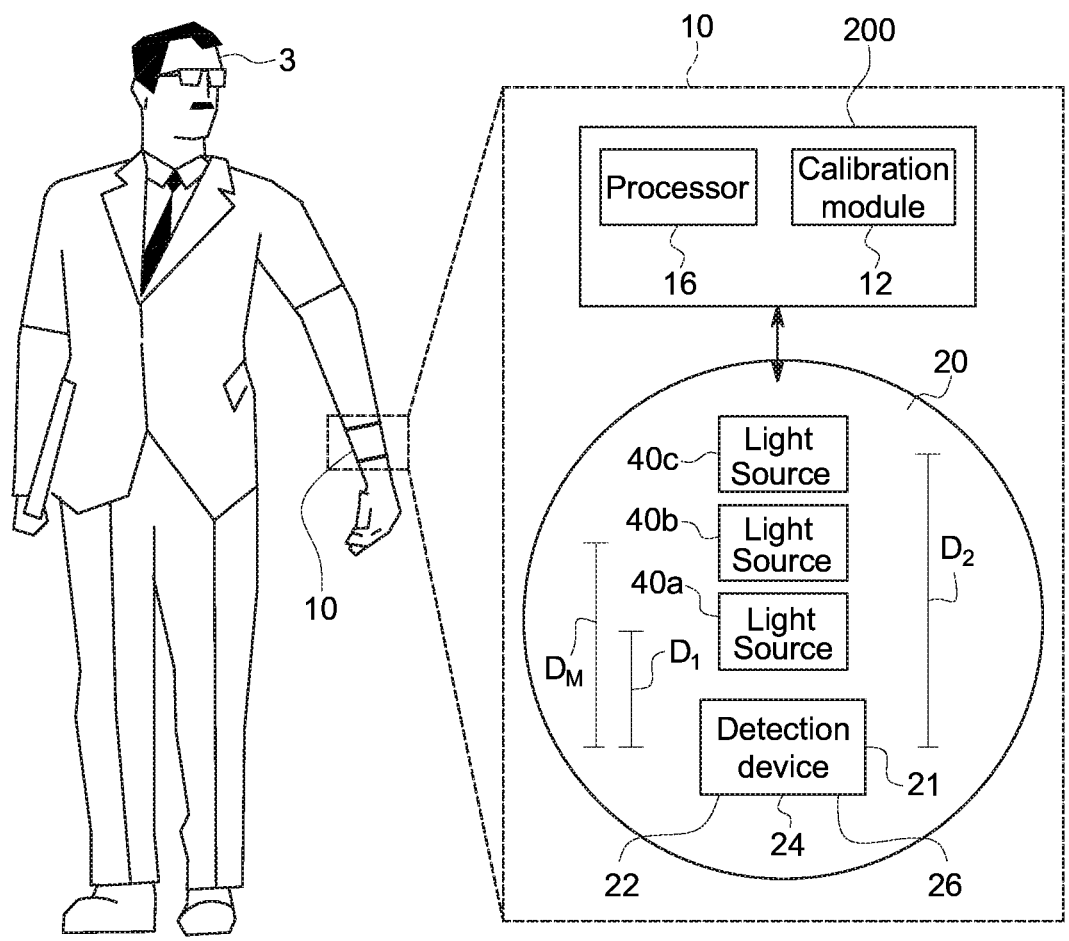

FIGS. 1A and 1B depict two different embodiments of the reflective $SpO_2$ sensor 20. In the arrangement of FIG. 1A, the reflective $SpO_2$ sensor 20 comprises three separate detection devices 21a, 21b, 21c. A first detection device 21a forms the close detector 22, a second detection device 21b forms the middle detector 24, and a third detection device 21c forms the far detector 26, which are arranged at increasing distances $D_1$, $D_M$, $D_2$, respectively, from a single light source 40. In the arrangement of FIG. 1B, the reflective $SpO_2$ sensor 20 comprises one detection device 21 forming the close detector 22, the middle detector 24, and the far detector 26. There, three separate light sources 40a, 40b, 40c are arranged at increasing distances $D_1$, $D_M$, $D_2$, respectively, from the single detection device 21. Accordingly, the same general effect is achieved using three light sources 40a, 40b, 40c and one detection device 21 as with one light source 40 and three detection devices 21a, 21b, 21c.

Depending on the sensor 20 configuration, including the arrangement and strength of the light pulses, the distances $D_1$, $D_M$, $D_2$ may be different values. To provide one example for a sensor having two different detector distances, the first distance $D_1$ may be in the range of 3-12 mm (such as within a more narrow range of 5-7 mm), and the second distance $D_2$ may be in the range of 12-30 mm (such as within a more narrow range of 15-20 mm). One example of a sensor having three different detector distances, the first distance $D_1$ may be in the range of 3-6 mm (such as within a more narrow range of 5-6 mm), the middle distance $D_M$ may be in the range of 6-12-mm (such as 10 mm), and the second distance $D_2$ may be in the range of 12-30 mm (such as within a more narrow range of 15-20 mm). Each of the one or more detection devices 40 (40a, 40b, 40c) is, for example, a photodiode.

The light sensed by the far detector 26 will provide the best, most reliable measurement of arterial blood oxygenation, whereas the light measured at the close detector 22 will be comprised of substantially greater error factors, including light reflected from venous blood, tissue, skin, etc. Similarly, the light reflected to the middle detector 24 will be somewhere in between that of the close detector 24 and the far detector 26, and thus containing a greater error factor component than that sensed at the far detector 26 but less than the close detector 22. For the embodiment in FIG. 1A, when the light pulse is a high intensity light pulse, thus reaching all detectors including the far detector 26, then the error factor will be smaller than the error factor for the low intensity light pulse received only at the close detector 22. For the embodiment of FIG. 1B, the high intensity light pulse reaching the detection device 21, forming the far detector 26, will have a lower error factor than the low intensity light pulse reaching the detection device 21, forming the close detector 22.

A calibration factor can then be determined to isolate the error factor seen in the close detector 22 and/or the middle detector 24, as compared to the light reflection received at the far detector 26. The calibration factor is determined by comparing the light reflection sensed with the close detector 22 and/or the middle detector 24 with that sensed by the far detector 26. In the embodiment of FIG. 1A, the reflection of the high intensity light pulse by the single light source 40 is sensed with the close detector 21a, 22 and/or the middle detector 21b, 24 is compared with that sensed by the far detector 21c, 26. In the embodiment of FIG. 1B, a low intensity light pulse and a high intensity light pulse are separately emitted by the first light source 40a, and the third light source 40c, respectively, in close time proximity. The two different light pulses are then received at the detection device 21, which acts at separate times as the close detector 22 and the far detector 26, respectively. The received close and far light reflections can then be compared to one another. The calibration factor is utilized to isolate the error factors in the light sensed at the close detector 22 and/or the middle detector 24, thus increasing the reliability and feasibility of measuring $SpO_2$ with a lower intensity light pulse. Once the calibration factor is determined, a lower intensity light pulse can be utilized and sensed at the close detector 22 and or the middle detector 24. The lower intensity light pulse requires substantially less energy to generate than the high intensity light pulse, and thus significant energy savings can be gained by measuring the patient's $SpO_2$ using the low intensity light pulse.

In certain embodiments, the error factor in the close detector 22 may be too great, such that measurement from the close detector 22 is not sufficiently reliable. Such a situation may exist, for example, where significant fatty or muscle tissue resides at the measurement site, or there is no artery between the light source 40 and the respective detection device 22, 24, 26. In certain embodiments, the middle detector 24 may be utilized in conjunction with a medium intensity light pulse to measure the $SpO_2$ instead of the close detector 22 and the low intensity light pulse. There, the calibration factor is calculated to isolate the error factor in the middle detector 24, such as based on a difference between light sensed by the middle detector 24 and the far detector 26. While utilizing more energy than the low intensity light pulse, the medium intensity light pulse still requires significantly less energy than the high intensity light pulse, and thus continuous or periodic $SpO_2$ measurements can be reliably made with a reduced power consumption utilizing the calibration factor.

In other embodiments, the close detector 22 may not provide sufficient arterial blood measurement. In situations where there are no major arteries present between the relevant light source 40 and the close detector 22, and thus the close detector 22 is at a location where an accurate $SpO_2$ measurement cannot be obtained, the system 10 may be configured to perform an assessment to see if the middle detector 24 is better located to perform the measurement. Thus, where the error factor is too high due to the lack of an artery at the location of the first detector 22, the system will try the second detector 24 to see if an artery is present and the error factor is sufficiently low. Thereby, the system 10 is configured to take advantage of the presence of the multiple detectors 22, 24, 26, where the probability of having artery directly beneath at least one detectors increases with the number of detectors.

Accordingly, ongoing measurements of $SpO_2$ from a patient can be utilized in a low power mode, such as with a low intensity light pulse and the close detector 22 or a medium intensity light pulse and the middle detector 24. However, over time the calibration factor may become inaccurate and outdated due to physiological changes at the measurement site. For example, profusion to the measurement site may change over time due to a change in the patient's activity, physician, body temperature, etc. Accordingly, the calibration factor may be recalculated, either periodically or when the measurement in the lower power mode becomes unreliable. The system 10 switches into a high power mode for the recalibration, generating the high intensity light pulse (and in certain embodiments also the low intensity light pulse) and determining the calibration factor be comparing the light reflection detected by the close detector 22 and/or the middle detector 24 to that received at the far detector 26. Once the calibration factor is reestablished, the system 10 switches back into the low power mode in order to determine the running $SpO_2$ measurement. Thereby, reliable reflective $SpO_2$ measurement can be obtained using a fraction of the energy amount required by current reflective $SpO_2$ sensors. In certain embodiments, calibration may be re-performed, either periodically (e.g., at 5 minute intervals) or when the accuracy of the $SpO_2$ measurement degrades (such as based on a change in the environment or the patient's condition). Accordingly, the system 10 would switch back to a high power mode, perform the calibration, and then (assuming that the patient condition has not deteriorated) would return to the low power mode for continued measurement using the updated calibration value.

FIGS. 1A and 1B schematically depict exemplary embodiments of a reflective $SpO_2$ measurement system 10. In the depicted embodiment, the reflective $SpO_2$ measurement system 10 is a wrist-worn device, such as a bracelet or a watch, comprising the $SpO_2$ sensor device 20 and computing system 200 that controls the function of the $SpO_2$ sensor device 20 and receives sensed information therefrom. In other embodiments, the reflective $SpO_2$ measurement system may be a different body-worn device, such as one that attaches to and measures at the patient's forehead, chest, foot, etc. The $SpO_2$ sensor device 20 includes at least two light detectors, including a close detector 22 and a far detector 26. As described above, the sensor device 20 may further include a middle detector 24 between the close detector 22 and the far detector 26. The detectors 22, 24, 26 are positioned to sense reflected light emitted from light source 40. Specifically, the close detector 22 is positioned closest to the light source 40 at a first distance $D_1$ from the light source 40. The far detector 26 is positioned farthest from the light source 40 at a second distance $D_2$ from the light source 40. In embodiments comprising a middle detector, the middle detector 24 is positioned at a middle distance $D_M$ from the light source 40, between the close detector 22 and the far detector 26.

During calibration mode, the output signals from the detectors 22, 24, 26 are received by the calibration module 12 within the computing system 200. The calibration module 12 includes a set of software instructions executable on the processor 16 to receive the signals from the detectors 22, 24, 26 and calculate the calibration factor based thereon. For example, the calibration module 12 may be configured to execute an algorithm to compare the light sensed by the close detector 22 and/or the middle detector 24 against that sensed by the far detector 26 to isolate the part of the reflected light caused by error factors, such as light reflection from venous blood, skin, subcutaneous tissue, fat, muscle, etc.

In other embodiments, the calibration module may include or employ a neural network configured to output the calibration factor based on the outputs of the detectors 22, 24, 26. For example, the neural network may be initially trained to output calibration factors for a range of standard detector inputs, and may be configured to adapt to the particular patient measurement location based on several measurement cycles from the various detectors 22, 24, 26. In other embodiments, the calibration module 12 may comprise a neural network configured to be trained upon initial connection of the reflective $SpO_2$ measurement system 10 to the patient by receiving an additional input from another $SpO_2$ sensor on that patient, such as a standard finger-mounted $SpO_2$ sensor used as a training input that can be correlated to measurements from the detectors 22, 24, 26. Thereby, the neural network can be trained to isolate the error factor utilizing the additional $SpO_2$ measurement from the finger-mounted device.

The one or more light sources 40 can be any light source appropriate for generating the at least two wavelengths required for $SpO_2$ measurement. In certain embodiments, each light source 40 may be comprised of one or more sets of LEDs. For example, each set of LEDs may include at least an infrared LED and a red LED, and/or and LED in the spectrum used for near infrared spectroscopy (NIR) (e.g., ranging from 700 to 1100 nm). The LED sets may be configured such that the lumen output of the LEDs is controlled via dynamic current scaling, where a higher current is provided to the LEDs in order to raise the intensity of the light pulse for the SpO$_2$ measurement. Additionally, the intensity of the light pulse may be increased by activating more than one set of LEDs. For example, the light source 40 may include three LED sets 41, 46, 48 that are separately activatable to increase the intensity of the light pulse. In one exemplary embodiment, the low intensity light pulse may be generated by the first LED set 41, the medium intensity light pulse may be generated by activating both the first and second LED sets 41, 46, and the high intensity light pulse may be generated by activating all three LED sets 41, 46, 48. In other embodiments, the various intensity light pulses may be generated by varying the current to one or two LED sets. As discussed above, the amount of light required to reach the far detector is exponentially more than that required to reach the close detector. Thus, depending on the configuration of the LED sets, the low intensity light pulse and the medium intensity light pulse may both be generated by varying the current to the first LED set 41. The second and third LED sets 46-48 may be required to generate the high intensity light pulse, which is typically required to be ten to sixteen times more light than the low intensity light pulse required to reach the close detector. Where multiple light sources 40 are provided, such as in the embodiment shown at FIG. 1B, the light sources 40a-40c may each be configured to generate the respective light intensity needed by that source (e.g., the first light source 40a is optimized to generate the low intensity light pulse, the second light source 40b is optimized to generate the medium intensity light pulse, and the third light source 40c is optimized to generate the high intensity light pulse).

Each light source 40 emits two or more wavelengths of the light, which may be at various intensities as is described above. While each light source emits only one wavelength at one time, the frequency emissions are toggled at a fast enough frequency such that variation in measurement due to a physiological change in the measurement area over time is not a factor. The different frequencies are then scanned in sequence—e.g., infrared—red—green. This sequence is repeated at a high frequency, for example, 100 times per second. In one embodiment, the light source 40 emits three different wavelengths of light, including an infrared wavelength, a red wavelength, and a third wavelength. In certain embodiments the third wavelength is shorter than the red visible light range. For example, the third wavelength may be in the green range of visible light. In other embodiments, the third wavelength is longer than the red range, such as near infrared. For example, the third wavelength may be in the range used for NIRS, such as in the range of 7001100 nm. Each wavelength has differing properties regarding how they scatter and transmit through tissue. The shorter wavelengths, such as the green light, are more readily reflected by the superficial tissue than the longer wavelengths, such as red, near infrared, and infrared. Conversely, the longer wavelengths are transmitted through tissue more easily, and thus penetrate deeper into the tissue before being reflected.

Figure 2:
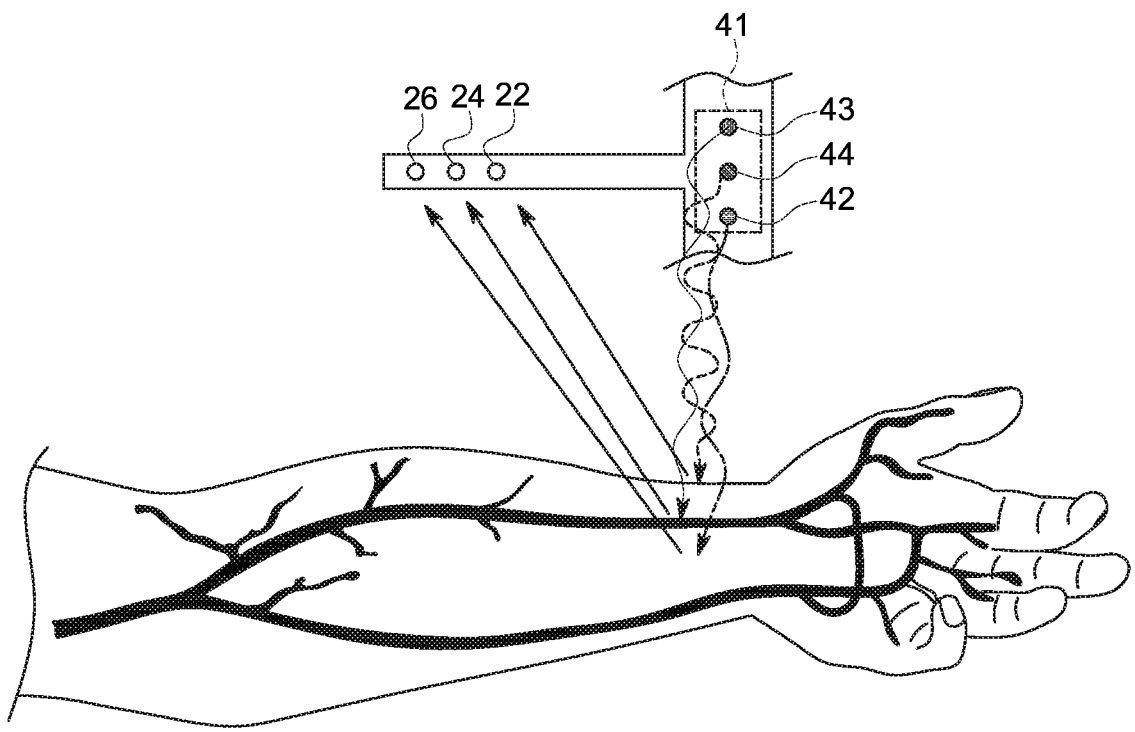
FIG. 2 schematically depicts reflective $SpO_2$ measurement utilizing an LED set emitting three different light wavelengths and three different detectors are various distances from the light source.

FIG. 2 depicts an exemplary embodiment of a light source, and specifically a first LED set 41 having three LEDs, including an infrared LED, a red LED, and a green LED. The light from the three LEDs is reflected by the tissue at various depths in the measurement site and is received at the three detectors, including the close detector 22, the middle detector 24, and the far detector 26. Portions of each of the three LEDs may be received at each of the three detectors 22, 24, 26, but only one arrow is shown pointing to each detector representing all of the light reflected towards that detector (for visual clarity and readability). Given that the green wavelength is generally reflected by the skin and superficial tissue, most of the green light is received at the close detector 22. Some of the red and infrared light is also superficially reflected, or is reflected at angles such that it is also received at the close detector 22. However, much of the red and infrared light will penetrate deeper into the measurement location and penetrate the arteries in order to allow for measurement of the arterial blood oxygenation. Most of the light that penetrates the arteries will reflect to the more distant detectors 24 and 26, and particularly the far detector 26. Accordingly, the amount of light received at the close detector 22 that contains information about the arterial blood oxygenation is relatively small compared to the light reflected by other tissue. This is where the calibration factor comes in, which can allow the separation of the arterial blood oxygenation measurements from the error factor. The green wavelength helps to isolate the contribution by the skin and venous blood, as it is generally superficially reflected.

Figure 3:
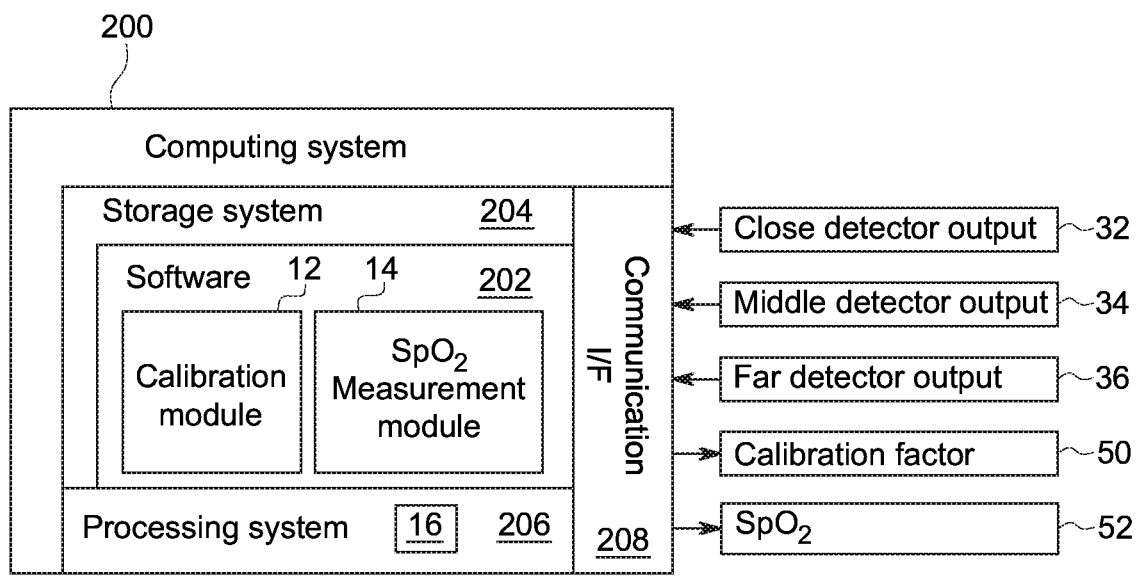
FIG. 3 schematically depicts a computing system according to the present disclosure.

FIG. 3 provides a schematic diagram of an exemplary computing system for reflective SpO$_2$ measurement as disclosed herein, including having a calibration module 12 and an SpO$_2$ measurement module 14. Namely the calibration module 12 calculates a calibration factor 50 based on outputs from the detectors 22, 24, 26 resulting from a high intensity light pulse. The close detector output 32 and/or the middle detector output 34 are compared to the far detector output 36 in order to calculate a calibration factor that can be used to isolate the error factor expected at that particular measurement site. That calibration factor 50 is then utilized to allow determination of the patient's SpO$_2$ when operating in the low power mode—i.e., with a low intensity light pulse (or a medium intensity light pulse if the low intensity light pulse contains greater than a threshold error factor). For example, an SpO$_2$ measurement module 14 utilizes the most recent calibration factor 50 to calculate the SpO$_2$ in the low power mode. In certain embodiments, the SpO$_2$ calculation function and the calibration factor calculation function are provided by a single module, or set of software instructions, performing all of the functions described herein.

The computing system 200 that includes a processing system 206, storage system 204, software 202, communication interface 208 and a user interface 210. The processing system 206 loads and executes software 202 from the storage system 204, including calibration module 12 and the SpO$_2$ measurement module 14. Each of the modules 12 and 14 include computer-readable instructions that, when executed by a processor, direct operation as described in herein in further detail, including to calculate a calibration factor 50 and utilize that calibration factor 50 to measure the patient's SpO$_2$ in a low power mode.

Although the computing system 200 as depicted in FIG. 3 includes one software 202 encapsulating one calibration module 12 and one SpO$_2$ measurement module 14, it should be understood that one or more software elements having one or more modules may provide the same operation. Similarly, while description as provided herein refers to a computing system 200 and a processing system 206, it is to be recognized that implementations of such systems can be performed using one or more hardware sets, including one or more processors 16, which may be remotely located from one another and communicatively connected, and such implementations are considered to be within the scope of the description.

The processing system 206 includes the processor 16, which may be a microprocessor, a general purpose central processing unit, an application-specific processor, a microcontroller, or any other type of logic-based device. The processing system 206 may also include circuitry that retrieves and executes software 202 from storage system 204. Processing system 206 can be implemented within a single processing device but can also be distributed across multiple processing devices or sub-systems that cooperate in executing program instructions.

The storage system 204 can comprise any storage media, or group of storage media, readable by processing system 206, and capable of storing software 202. The storage system 204 can include volatile and non-volatile, removable and non-removable media implemented in any method or technology for storage of information, such as computer-readable instructions, data structures, program modules, or other data. Storage system 204 can be implemented as a single storage device but may also be implemented across multiple storage devices or sub-systems Examples of storage media include random access memory, read only memory, optical discs, flash memory, virtual memory, and non-virtual memory, magnetic sets, magnetic tape, magnetic disc storage or other magnetic storage devices, or any other medium which can be used to store the desired information and that may be accessed by an instruction execution system, as well as any combination or variation thereof, or any other type of storage medium. Likewise, the storage media may be housed locally with the processing system 206, or may be distributed in one or more servers, which may be at multiple locations and networked, such as in cloud computing applications and systems. In some implementations, the storage media can be a non-transitory storage media. In some implementations, at least a portion of the storage media may be transitory.

The communication interface 208 interfaces between the elements within the computing system 200 and external devices, such as the light detectors 22, 24, and 26.

Figure 4:
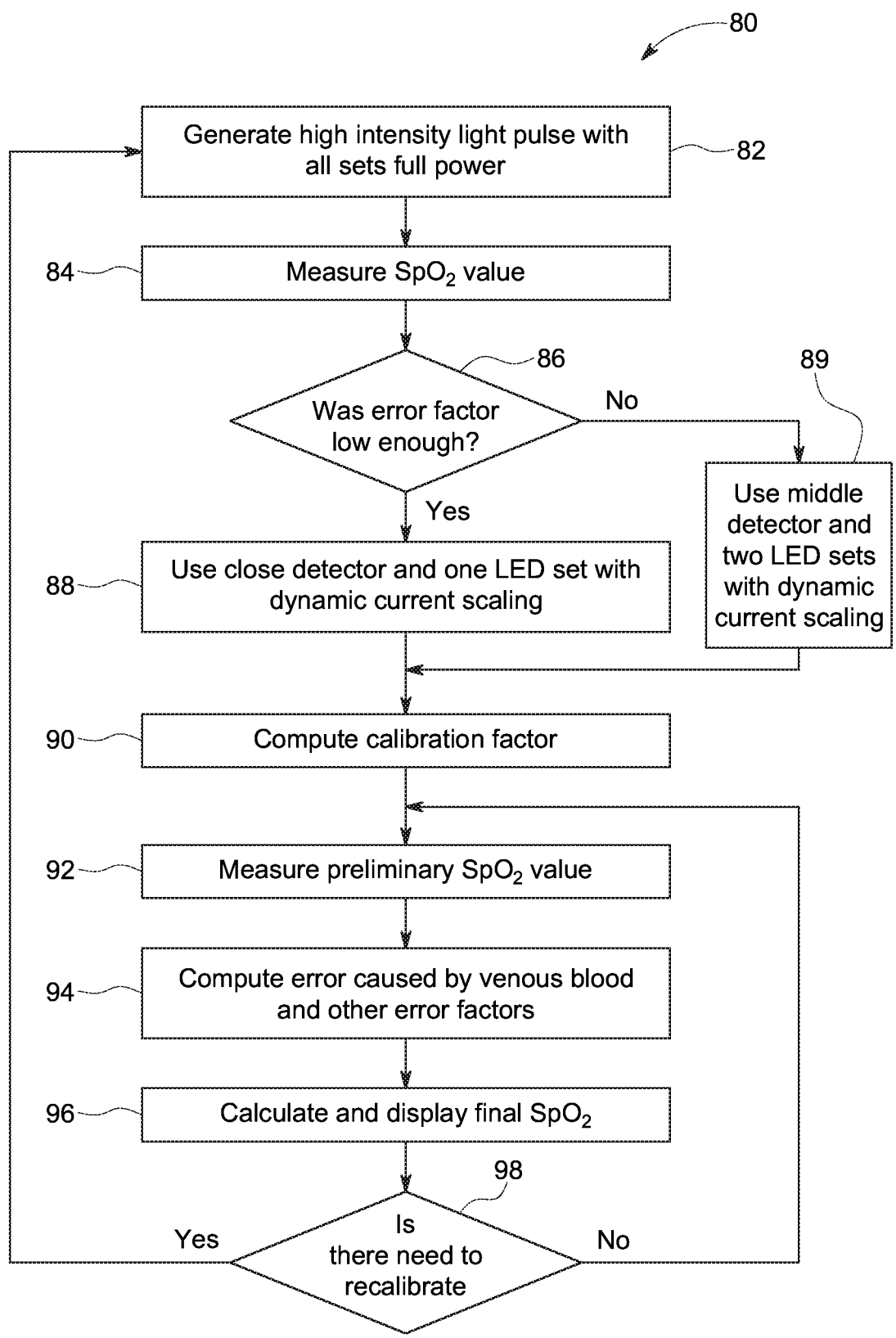
FIG. 4 is a flow chart depicting an exemplary method of reflective $SpO_2$ measurement according to the present disclosure.

FIG. 4 depicts one embodiment of a method 80 of reflective $SpO_2$ measurement. To begin, a high intensity light pulse is generated at step 82, such as using all LED sets at full power. The $SpO_2$ value is calculated at step 84 based on the output of the light detectors, and especially the light measurement of the far detector 26. At step 86, logic is executed to determine whether the error factor is sufficiently low such that the close detector 22 can be utilized for the low power measurement. For example, the error factor may be determined, as described herein, based on the differences in the light measurements at the at least two (and possible three or more) distances, using the difference as the error factor.

If the error factor is less than the threshold value, such as less than a threshold value, then step 88 is executed to operate in a low power mode using the close detector 22 and only one LED set to generate a low intensity light pulse and measure $SpO_2$ therefrom. If the error factor in the close detector 22 is greater than or equal to the threshold value, the middle detector may be utilized and a medium light pulse generated, such as using two LED sets with dynamic current scaling (represented at step 89). The calibration factor is computed at step 90, such as a set of coefficients correlating either the close detector 22 output to the far detector 26 output, or the middle detector 24 output to the far detector 26 output, depending on which detector is being utilized in the low power mode.

The $SpO_2$ value is then measured in the low power mode at step 92 (either using the low intensity light pulse and the close detector 22, or the medium intensity light pulse and the middle detector 23). For each measurement, the error caused by the venous blood and/or other error factors is calculated at step 94 based on the calibration factor. A final $SpO_2$ measurement is calculated, removing the contribution caused by the error factors. The $SpO_2$ measurement is displayed at step 96, such as on a user interface associated with the system 10.

Steps are executed at step 98 to determine whether recalibration is needed. For example, recalibration may occur every predetermined time interval. Alternatively, recalibration may be dictated based on the error factor or based on another reliability measure of the $SpO_2$ calculation in the low power mode. For example, recalculation of the calibration factor 50 may be instructed when the $SpO_2$ measurement in the low power mode changes by more than a predetermined amount or otherwise falls outside of an acceptable measurement range, which indicates that the $SpO_2$ measurement in the low power mode may no longer be reliable. If recalibration is not needed, then the $SpO_2$ measurement continues in the low power mode. If recalibration is needed, then the method returns to step 82 where it operates in the high power mode to make a more reliable $SpO_2$ measurement and recalculate the calibration factor 50.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:

1. A reflective $SpO_2$ measurement system comprising:
   at least one light source that emits light of at least a first wavelength and a second wavelength, wherein the second wavelength is shorter than the first wavelength;
   one or more detection devices forming a close detector positioned at first distance from the light source and a far detector positioned at second distance from the light source, wherein the second distance is greater than the first distance;
   wherein the $SpO_2$ measurement system is configured to operate in a high power mode to determine a calibration factor based on a comparison of light reflections detected by the close detector and the far detector;
   wherein the $SpO_2$ measurement system is configured to operate in a low power mode to:
      generate a low intensity light pulse with the light source, wherein the low intensity light pulse contains light of the first and second wavelengths;
      detect a close reflection of the low intensity light pulse with the close detector; and
      determine an $SpO_2$ based on the close reflection of the low intensity light pulse and the calibration factor.

2. The system of claim 1, further comprising:
   a calibration module executable on a processor during operation in the high power mode to:

control the light source to generate a high intensity light pulse;
detect a far reflection of the high intensity light pulse with the far detector;
detect a close reflection of the high intensity light pulse with the close detector; and
calculate the calibration factor based on the far reflection and the close reflection of the high intensity light pulse.

3. The system of claim 2, wherein the calibration module comprises a neural network trained to output the calibration factor based on inputs including the far reflection and the close reflection of the high intensity light pulse.

4. The system of claim 2, wherein the calibration module is activated to redetermine the calibration factor at a predefined interval.

5. The system of claim 2, wherein the calibration module is activated to redetermine the calibration factor when an error factor of the close reflection exceeds a threshold value.

6. The system of claim 2, further comprising a middle detector positioned at a middle distance from the light source, wherein the middle distance is between the first distance of the close detector and the second distance of the far detector, and wherein the calibration module is configured to:
detect a middle reflection of the high intensity light pulse with the middle detector; and
determine the calibration factor based further on the middle reflection.

7. The system of claim 6, wherein the system is further configured to operate in a medium power mode to:
generate a medium intensity light pulse with the at least one light source, wherein the medium intensity light pulse contains light of the first and second wavelengths;
detect a middle reflection of the medium intensity light pulse with the middle detector; and
determine an $SpO_2$ based on the middle reflection of the medium intensity light pulse and the calibration factor.

8. The system of claim 7, further comprising three light sources and one detection device forming the close detector, the middle detector, and the far detector;
wherein the close detector is formed by the detection device operating to receive light from a first light source generating the low intensity light pulse and positioned at the first distance from the detection device, the middle detector is formed by the detection device operating to receive light from a second light source generating the medium intensity light pulse and positioned at the middle distance from the detection device, and the far detector is formed by the detection device operating to receive light from a third light source generating the high intensity light pulse and positioned at the second distance from the detection device.

9. The system of claim 7, further comprising one light source and three detection devices; and
wherein the close detector is formed by a first detection device positioned the first distance from the one light source and operating to receive the low intensity light pulse therefrom, the middle detector is formed by a second detection device positioned the middle distance from the one light source and operating to receive the medium intensity light pulse therefrom, and the far detector is formed by a third detection device positioned the second distance from the one light source and operating to receive the high intensity light pulse therefrom.

10. The system of claim 9, wherein the one light source comprises a first set of LEDs, a second set of LEDs, and a third set of LEDs; and
wherein each set of LEDs emits light of at least the first wavelength and the second wavelength, wherein the low intensity light pulse is generated by the first set of LEDs, the medium intensity light pulse is generated by the first and the second set of LEDs, and the high intensity light pulse is generated by the first, the second, and the third set of LEDs.

11. The system of claim 10, wherein each set of LEDs contains at least a red LED, an infrared LED, and a green LED.

12. A method of reflective $SpO_2$ measurement, the method comprising:
generating at least one light pulse with at least one light source, wherein the at least one light pulse includes at least a first light wavelength and a second light wavelength, wherein the second wavelength is shorter than the first wavelength;
detecting a close reflection of the at least one light pulse with a close detector positioned at a first distance from one of the at least one light source;
detecting a far reflection of the at least one light pulse with a far detector positioned at a second distance from one of the at least one light source, wherein the second distance is greater than the first distance;
calculating a calibration factor based on the far reflection and the close reflection of the at least one light pulse;
generating a low intensity light pulse with the at least one light source, wherein the low intensity light pulse contains light of the first and second wavelengths;
detecting a close reflection of the low intensity light pulse with the close detector; and
determining an $SpO_2$ based on the close reflection of the low intensity light pulse and the calibration factor.

13. The method of claim 12, further comprising redetermining the calibration factor at a predefined interval.

14. The method of claim 12, further comprising:
calculating an error factor for the close reflection of the low intensity light pulse; and
redetermining the calibration factor when the error factor exceeds a threshold value.

15. The method of claim 12, wherein each of the at least one light source further emits a third wavelength.

16. The method of claim 15, wherein the first wavelength is infrared light, the second wavelength is red light, and the third wavelength is green light.

17. The method of claim 12, wherein the at least one light source comprises three light sources, and one detection device forms the close detector, the middle detector, and the far detector;
wherein the close detector is formed by the detection device operating to receive light from a first light source generating the low intensity light pulse and positioned at the first distance from the detection device, the middle detector is formed by the detection device operating to receive light from a second light source generating a medium intensity light pulse and positioned at a middle distance from the detection device, and the far detector is formed by the detection device operating to receive light from a third light source generating a high intensity light pulse and positioned at a second distance from the detection device;

wherein the step of generating at least one light pulse with one or more light sources for determining the calibration factor further comprises:
  generating the low intensity light pulse with the first light source and measuring the close reflection;
  generating the high intensity light pulse with the far detector and measuring the far reflection; and
wherein the calibration factor is determined based on the close reflection of the low intensity light pulse and the far reflection of the high intensity light pulse.

18. The method of claim 12, further comprising:
detecting a middle reflection of a high intensity light pulse with a middle detector, positioned at a middle distance from the at least one light source, wherein the middle distance is between the first distance of the close detector and the second distance of the far detector; and
determining the calibration factor based further on the middle reflection.

19. The method of claim 18, further comprising:
determining that an error factor of the close reflection of the low intensity light pulse is too high;
generating a medium intensity light pulse with the at least one light source, wherein the medium intensity light pulse contains light of the first and second wavelengths;
detecting a middle reflection of the medium intensity light pulse with the middle detector; and
determining the $SpO_2$ based on the middle reflection of the medium intensity light pulse and the calibration factor.

20. The method of claim 19, wherein the light source comprises multiple sets of two or more LEDs, and wherein the low intensity light pulse is generated by powering a first set of LEDs, the medium intensity light pulse is generated by powering the first set of LEDs and a second set of LEDs, and the high intensity light pulse is generated by powering the first, the second, and a third set of LEDs.

* * * * *